(12) United States Patent
Kuebler et al.

(10) Patent No.: US 9,144,517 B2
(45) Date of Patent: Sep. 29, 2015

(54) OPHTHALMIC SURGICAL SYSTEM AND A CONTROL APPARATUS THEREFOR

(71) Applicant: Carl Zeiss Meditec AG, Jena (DE)

(72) Inventors: Christoph Kuebler, Oberhochen (DE); Wolfram Wehner, Nuremberg (DE); Karlheinz Rein, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 33 days.

(21) Appl. No.: 13/854,075

(22) Filed: Mar. 30, 2013

(65) Prior Publication Data

US 2013/0261637 A1     Oct. 3, 2013

Related U.S. Application Data

(63) Continuation of application No. PCT/DE2011/001775, filed on Sep. 24, 2011.

(30) Foreign Application Priority Data

Sep. 30, 2010  (DE) .......................... 10 2010 047 012

(51) Int. Cl.
    *A61F 9/00*     (2006.01)
    *A61F 9/007*    (2006.01)
    *A61M 1/00*     (2006.01)

(52) U.S. Cl.
    CPC .......... *A61F 9/00745* (2013.01); *A61M 1/0058* (2013.01)

(58) Field of Classification Search
    CPC ............ A61F 9/00745; A61F 9/00763; A61F 9/00736; A61F 2009/00887; A61M 1/0058
    USPC ......... 606/107, 161, 162, 166, 167, 168, 169, 606/170, 171; 604/22
    See application file for complete search history.

(56) References Cited

U.S. PATENT DOCUMENTS 6,179,805 B1 *  1/2001  Sussman et al. ................ 604/27
6,544,254 B1    4/2003  Bath
(Continued)

FOREIGN PATENT DOCUMENTS

WO    WO 2005/092023    10/2005

OTHER PUBLICATIONS

International Search Report dated Mar. 26, 2012 of international application PCT/DE2011/001775 on which this application is based.
(Continued)

*Primary Examiner* — Jonathan W Miles
(74) *Attorney, Agent, or Firm* — Walter Ottesen P.A.

(57) ABSTRACT

A control device for an ophthalmic surgical system includes a flow determination device for determining an actual value of fluid flow in an aspiration line. The aspiration line is coupled to a handpiece for phacoemulsification of an eye lens and an occlusion determination device determines whether there is an occlusion because of a particle of the eye lens at a suction opening of the aspiration line. An evaluation unit establishes a hardness of the particle in dependence on the determined actual value of the fluid flow in the aspiration line should the occlusion determination device have determined that an occlusion is present, and, dependent on the hardness, determines a first value of ultrasound energy, which can be supplied to the handpiece by an energy source. A control unit actuates the energy source, during the occlusion, so that it outputs the determined first value of the ultrasound energy.

8 Claims, 2 Drawing Sheets

(56) References Cited

U.S. PATENT DOCUMENTS

| | | | |
|---|---|---|---|
| 6,962,583 B2* | 11/2005 | Kadziauskas et al. | ............ 606/6 |
| 8,277,462 B2 | 10/2012 | Heymann et al. | |
| 2004/0267136 A1 | 12/2004 | Yaguchi et al. | |
| 2005/0209560 A1 | 9/2005 | Boukhny et al. | |

OTHER PUBLICATIONS

English translation of the Office action of the German Patent Office dated Apr. 7, 2011 in German patent application 10 2010 047 012.0 on which the claim of priority is based.

* cited by examiner $$Q_{ACT} > 0 \frac{ml}{s}$$

$$Q_{ACT} \approx 0 \frac{ml}{s}$$

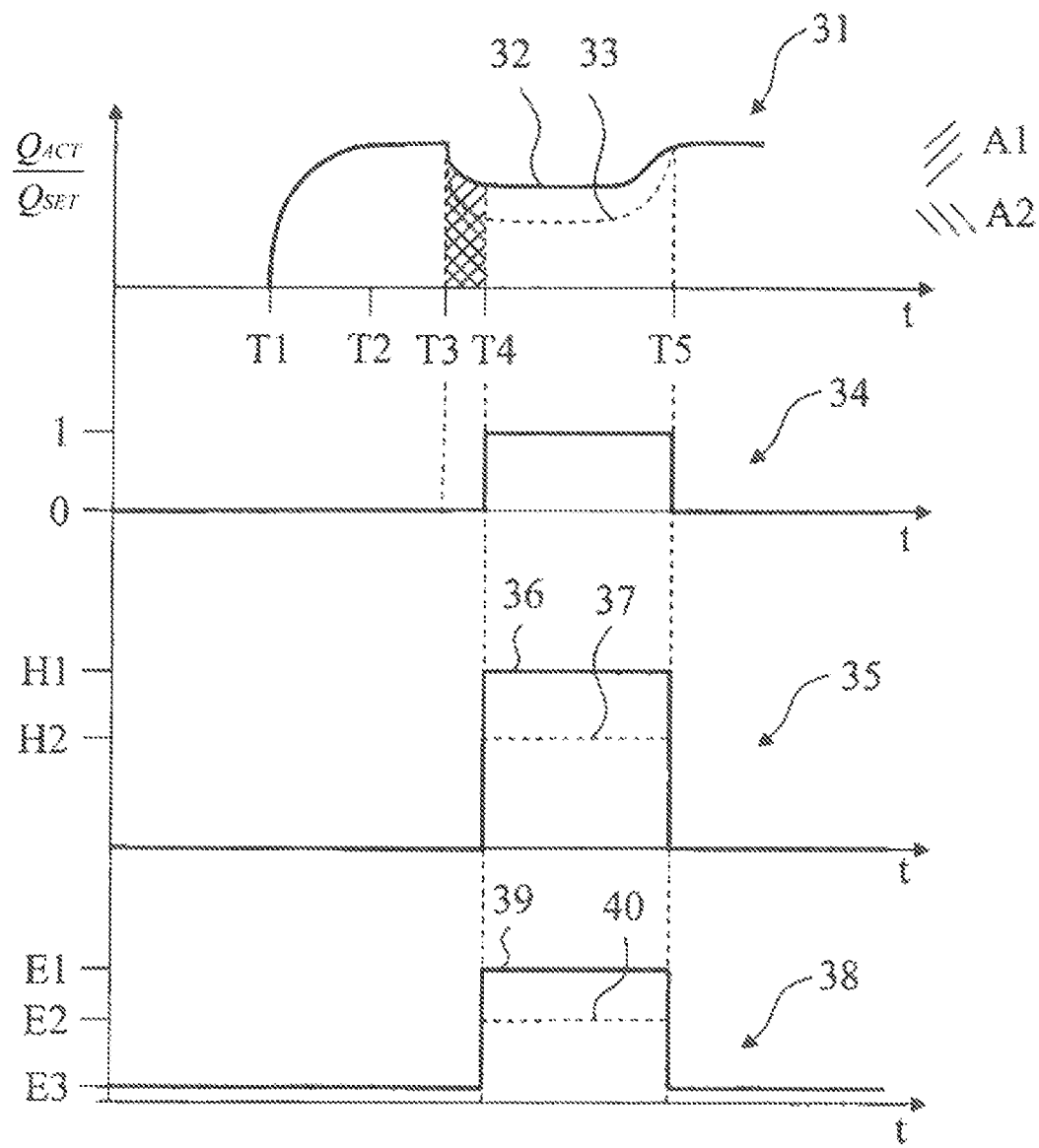

OPHTHALMIC SURGICAL SYSTEM AND A CONTROL APPARATUS THEREFOR

CROSS REFERENCE TO RELATED APPLICATIONS

This application is a continuation application of international patent application PCT/DE2011/001775, filed Sep. 24, 2011, designating the United States and claiming priority from German application 10 2010 047 012.0, filed Sep. 30, 2010, and the entire content of both applications is incorporated herein by reference.

FIELD OF THE INVENTION

The invention relates to a control apparatus for an ophthalmic surgical system, dependent on an occlusion, and an ophthalmic surgical system with such a control apparatus.

BACKGROUND OF THE INVENTION

There are a number of surgical techniques for treating clouding within the eye lens, which is referred to as a cataract in medicine. The most common technique is phacoemulsification, in which a thin needle is introduced into the diseased lens and excited to vibrate by means of ultrasound. The vibrating needle emulsifies the lens in the direct vicinity thereof in such a manner that the created lens particles can be suctioned away through a line via a pump. In the process, a rinsing fluid (irrigation fluid) is supplied, with the particles and the fluid being suctioned away through an aspiration line. Once the lens has been completely emulsified and removed, a new artificial lens can be inserted into the empty capsular bag, and so a patient treated in this manner regains good visual acuity.

During emulsification, a particle can be suctioned toward the suction opening of the aspiration line in a vibrating needle in such a manner that the aspiration line is blocked. Such a state is referred to as occlusion. In this case, neither fluid nor any other broken-up lens particles can reach the aspiration line anymore. If a suction pump continues to operate in an unchanged manner, strong negative pressure builds up in the aspiration line. In general, the negative pressure does not suffice for suctioning the particles blocking the needle tip through the aspiration line. One option for terminating the occlusion is to operate the needle with higher ultrasound energy such that the particle at the needle tip breaks into smaller particles and the occlusion is terminated. However, the higher energy input for breaking up lens particles leads to the unwanted effect that the needle also strongly heats up the surrounding tissue. Since the needle is pierced through the cornea during the operation, this heats up the cornea and so the latter is also damaged (cornea burn) in the case of too long and high energy input into the eye lens. Such an injury to a patient's eye can foe avoided if the ultrasound energy required for breaking up particles is set to a low value for a relatively long period of time. However, this increases the length of the operation.

SUMMARY OF THE INVENTION

It is an object of the invention to provide a control apparatus for an ophthalmic surgical system via which phacoemulsification of the whole eye lens can be carried out in a short period of time, with risk of damage to the patient's eye being kept low. It is furthermore an object to provide an ophthalmic surgical system with such a control apparatus.

The control apparatus according to the invention for an ophthalmic surgical system includes:
  a flow determination device, by means of which an actual value of a fluid flow in an aspiration line can be determined, wherein the aspiration line is coupled to a handpiece for phacoemulsification of an eye lens;
  an occlusion determination device, by means of which it is possible to determine whether there is an occlusion as a result of a particle of the eye lens at a suction opening of the aspiration line;
  an evaluation unit, which is suitable for establishing a hardness of the particle of the eye lens dependent on the determined actual value of the fluid flow in the aspiration line should the occlusion determination device have determined that an occlusion is present, and, dependent on the hardness, for determining a first quantity of ultrasound energy, which can be supplied to a handpiece by means of an energy source; and,
  a control unit, by means of which the energy source can be actuated in such a way that, during the occlusion, it emits the established first quantity of the ultrasound energy.

The invention therefore proceeds from the concept of establishing a hardness of the eye lens depending on a determined actual value of the fluid flow in the aspiration line. According to the invention, it is possible, even using relatively low ultrasound energy, to produce lens particles having a sufficiently small dimension and to break up an occlusion if the hardness of the lens is relatively low. However, a higher quantity of ultrasound energy is required if the lens particles have a relatively high hardness. Thus, if it is possible to make a statement with respect to the hardness of the lens particles to be emulsified, it is possible, on the basis of such a hardness value, to set a maximum quantity of ultrasound energy made available. This avoids, for example, too much energy being supplied in the case of a soft lens particle, and so the risk of burning the cornea is reduced. If the whole eye lens only consists of relatively soft material, it suffices to operate the needle with a relatively low quantity of ultrasound energy. However, if the lens material consists partly of a hard and partly of a soft region, it is possible, by respectively determining the hardness of the lens particles to be broken up, to supply the ultrasound energy which is currently required for breaking up the particles. Such a control of ultrasound energy is substantially faster and more efficient than, for example, manual control using a foot pedal that needs to be actuated by the surgeon.

The control apparatus according to the invention also ensures that only a minimum required energy input is supplied for breaking up the respective particles. In the case of soft particles, little energy is supplied; more energy is supplied in the case of hard particles. This reduces the probability of injuring healthy tissue in the surroundings of the needle, such as the cornea, by overheating. Additionally, the energy is only supplied in the case where an occlusion has been identified. If the particles are so small that they can be suctioned through the aspiration line without problems, no ultrasound energy is supplied. This once again reduces the quantity of supplied energy and reduces the probability of injuring the patient's eye. Nevertheless, only little time is expended in breaking up the lens particles. Hence the addressed object is achieved by the control apparatus according to the invention.

In a preferred embodiment, the control unit is suitable for actuating the energy source in such a manner that it emits a second quantity of ultrasound energy should the occlusion determination device have determined that there is no occlusion present, wherein the second quantity is less than the first quantity. If there is no occlusion there are also no particles blocking the needle which need to foe broken up. Nevertheless, it may also be sensible to actuate the needle of the phacoemulsification handpiece with a low quantity of ultrasound energy without an occlusion being present. This can support the suctioning away and reproduce the transport of small particles according to the principle of a vibrating conveyor. If the second quantity of ultrasound energy is less than the first quantity of the ultrasound energy in the case of an occlusion, it is nevertheless possible to avoid the risk of damaging the patient's eye.

The occlusion determination device preferably has a measuring device for measuring the current used by an aspiration pump, or a pump power or the fluid flow in the aspiration line. If the particle blocks the needle, the aspiration pump can be driven in such a manner that it attempts still to suction the particle through the aspiration line by means of a higher negative pressure. In this case the current drawn by the pump increases, and so the current intensity in the pump forms a parameter for an occlusion. Naturally, the product of the drawn current and the applied pump voltage, that is the pump power, can also be used for detecting an occlusion. Alternatively, the occlusion determination device can also identify an occlusion from a fluid flow in the aspiration line. The fluid flow reduces significantly in the case of an occlusion.

According to one embodiment of the invention, the evaluation unit is configured for establishing the hardness of the lens particle depending on a quotient from dividing the actual value of the fluid flow by a predetermined intended value of the fluid flow. The surgeon can determine the intended value of the fluid flow before the start of a treatment. Such an intended value can depend on utilized pulse patterns in ultrasound energy supplied by pulses, or on mechanical dimensions of the needle of the phacoemulsification handpiece.

The evaluation unit is preferably configured for determining, over a predetermined period of time, an integral over time of the quotient from dividing the actual value of the fluid flow by the intended value of the fluid flow. Using this, it is possible to add quantities of such a quotient over a predetermined time. In the case of such an integration over a relatively long period of time, short-term tremor movements of the particle and strong variations in the fluid flow which accompany this no longer lead to hectic switching between a first quantity of ultrasound energy and a second quantity of ultrasound energy. Furthermore, by integrating the current quantities, it is possible to determine a hardness of the particle to be broken up in a more precise and reliable fashion.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
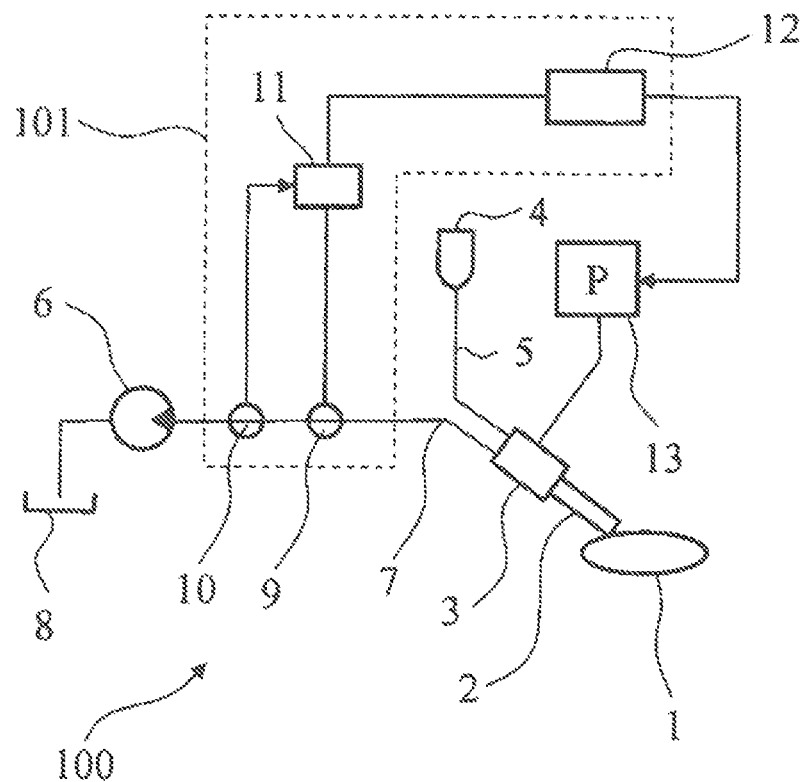
FIG. 1 is a schematic of a first embodiment of an ophthalmic surgical system with a control apparatus according to the invention.

FIG. 1 shows a schematic illustration of an embodiment of an ophthalmic surgical system 100 with a control apparatus 101. An eye lens 1 to be treated is worked upon by a needle 2 of a handpiece 3 during phacoemulsification. Irrigation fluid flows, from an irrigation fluid container 4, through an irrigation line 5 to the handpiece 3 and there to a needle 2, the tip of which touches the eye lens 1. The supplied irrigation fluid and the broken-up lens particles are suctioned away via an aspiration line 7, which leads to an aspiration pump 5 through the needle 2 and the handpiece 3. The fluid and the particles are then caught in an aspiration container 8. Coupled to the aspiration line is a through-flow determination device 9, via which it is possible to determine an actual value of a fluid flow. Furthermore, an occlusion determination device 10 is provided along with the aspiration line 7, wherein the former can be used to determine whether there is an occlusion by a particle of the eye lens 1 at the needle 2 of the handpiece 3. The occlusion determination device 10 can have a measuring device for determining a fluid flow in the aspiration line 7.

If the through-flow determination device 9 determines an actual value of a fluid flow in the aspiration line 7, this actual value can be fed to an evaluation unit 11, which establishes a hardiness of the particle of the eye lens to be broken up dependent on the determined actual value. If there is only a small reduction in the fluid flow such that a small part of the aspiration line 7 is still free at the tip of the needle 2 and fluid or very small particles can be suctioned through, only a relatively weak occlusion is present, but this is determined by the occlusion determination device 10. The inventors have observed that such a situation is present if a particle to be broken up is relatively hard. However, if the flow determination device establishes that the actual value is only relatively low, the inventors' experience suggests that a relatively soft particle is present.

Depending on the hardness, the evaluation unit 11 determines a first quantity of ultrasound energy with which the particle in front of the needle 2 should be acted upon. This information is fed to a control unit 12 via which it is possible to actuate an energy source 13 in such a manner that, during the occlusion, it emits the established first quantity of ultrasound energy to a handpiece 3.

Figure 2:
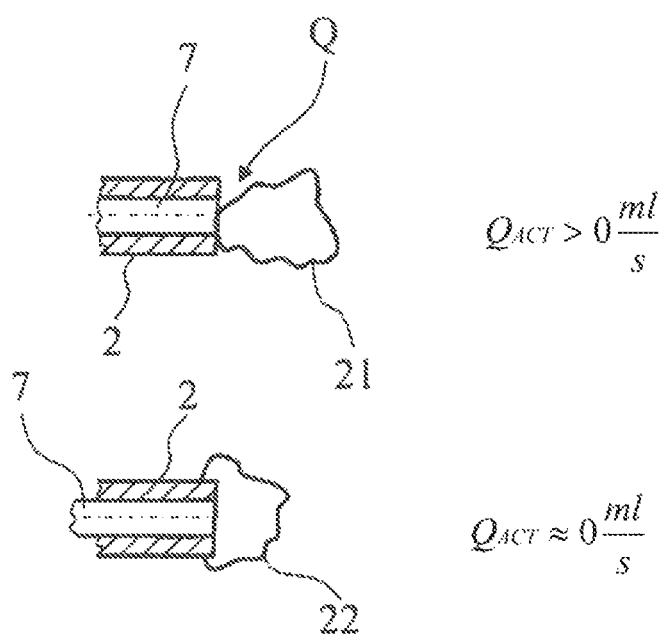
FIG. 2 is a schematic of a hard and a soft particle at the edge of a suction opening of a needle of a phacoemulsification handpiece; and, FIG. 3 is a diagram with curve profiles as a function of time for the following: a quotient from dividing an actual value of a fluid flow by a nominal value of a fluid flow; an occlusion; a hardness of a particle to be broken up; and, ultrasound energy.

FIG. 2 explains the situation at the tip of a needle if a hard particle 21 or a soft particle 22 is present. According to the observations of the inventors, in the case of a hard particle 21, there always remains a small area in the aspiration line 7 at the tip of the needle 2 through which fluid or very small particles can still be suctioned. The flow $Q_{ACT}$ is greater than zero. By contrast, in the case of a soft particle 22, the whole suction opening of the aspiration line 7 is blocked. Hence a fluid flow almost comes to a complete standstill in the case of a soft particle. A soft particle is completely suctioned toward the tip of the needle as a result of the suction pressure in the aspiration line. This elasticity is lacking in the case of a hard particle, and so a small area through which fluid can still be suctioned always remains. The quantity of such a fluid flow through the aspiration line or the quotient from dividing the actual value of a fluid flow by an intended value of a fluid flow can therefore form a basis from this for establishing a hardness of a particle to be broken up, and for thereupon setting the amount of energy required for breaking up this particle.

FIG. 3 shows, for a first embodiment of the control apparatus according to the invention, a plurality of curve profiles plotted as a function of time. The uppermost diagram 31 shows a curve profile of a quotient from dividing an actual value of a fluid flow $Q_{ACT}$ by a set value of a fluid flow $Q_{SET}$, plotted over time (t). The aspiration pump 6 is switched on at the time T1, and so a stationary value for the quotient from dividing the actual value of the fluid flow $Q_{ACT}$ by the set value of the fluid flow $Q_{SET}$ sets in until the time T2. If a particle 21 or 22 rests against the tip of the needle, the quotient from dividing the actual value of the fluid flow $Q_{ACT}$ by the set value of the fluid flow $Q_{SET}$ reduces. According to the first embodiment, T3 can be defined as the time at which such a reduction in the quotient starts. According to a second embodiment, T3 can be defined as the time at which the quotient from dividing $Q_{ACT}$ by $Q_{SET}$ smaller than a predetermined threshold.

The curve profile 32 shows that the quotient from dividing $Q_{ACT}$ by $Q_{SET}$ drops from time T3 to time T4. The period of time between T3 and T4 is either fixedly set in advance or can be determined by the user prior to the start of an ophthalmic surgical procedure. If, at the time T4, the value of the quotient from dividing the actual value of the fluid flow $Q_{ACT}$ by the intended value of the fluid flow $Q_{SET}$ is smaller than a predetermined threshold, the occlusion determination device 10 establishes from this that an occlusion is present, and so a signal jumps from 0 to 1, see diagram 34. In actual fact, an occlusion can already foe present from the time T3, but the control apparatus according to the invention only establishes at the time T4 whether the occlusion is present. In this embodiment of the control apparatus, the period of time between T3 and T4 is used by the evaluation unit 11 to calculate, for this period of time between T3 and T4, the integral of the quotient from dividing the actual value of the fluid flow $Q_{ACT}$ by the intended value of the fluid flow $Q_{SET}$ such that an area A1 is determined, see FIG. 3. Preceding trials have established a dependence between, firstly, an integral of the quotient from dividing the actual value of the fluid flow $Q_{ACT}$ by the intended value of the fluid flow $Q_{SET}$ and, secondly, a lens hardness. This dependence can be stored in a table, which can be accessed by the evaluation unit 11. Hence the evaluation unit 11 is able to establish, from the integral of $Q_{ACT}$ divided by $Q_{SET}$, or from the determined area A1, that a hardness H1 is present, see the curve profile 36 in diagram 35. As a result of this hardness H1, the evaluation unit 11 determines a first quantity E1 of ultrasound energy, see diagram 38 and, therein, the curve profile 39. The control unit 12 can then be used to actuate an energy source 13 in such a manner that the first quantity E1 of ultrasound energy is supplied to the handpiece 3.

However, if the quotient from dividing the actual value of a fluid flow $Q_{ACT}$ by a set value of a fluid flow $Q_{SET}$ drops to a relatively low value between time T3 and time T4, see curve 33 in diagram 31, the integral of the quotient over time yields a lower value, which corresponds to the area A2. Although the occlusion determination device 10 identifies that an occlusion is present, the evaluation unit 11, on the basis of, firstly, the relation from the quotient from dividing $Q_{ACT}$ by $Q_{SET}$ and, secondly, the lens hardness, establishes a hardness H2 which is lower than the hardness H1, see diagram 35 and, therein, curve profile 37. This means that the evaluation unit 11 establishes a first value E2 of ultrasound energy, which is lower than the first value E1 in the case of a hard lens particle. This is illustrated in diagram 38 by a curve profile 40. The evaluation unit 11 is coupled to a control unit 12 in such a manner that, during the occlusion, the control unit 12 actuates an energy source 13 in such a manner that the energy source 13 supplies the established first quantity E2 to the needle 2 of the handpiece 3.

If the quotient from dividing the actual value of a fluid flow $Q_{ACT}$ by the set value of the fluid flow $Q_{SET}$ assumes a quantity which occurred during the period of time from T2 to T3, see diagram 31, this time is defined as T5 according to the first embodiment. However, according to a second embodiment, the time T5 can be defined as the time at which the quotient from dividing $Q_{ACT}$ by $Q_{SET}$ assumes the quantify which lies above the threshold. At this time T5 there is no longer an occlusion, and this is identified by the occlusion determination device 10. As a result, the signal from the occlusion determination device 10 drops back down from 1 to 0, see diagram 34. From this time T5, the basis for establishing a hardness of a particle is lacking, and so the energy source is actuated in such a way that a second quantity E3 of ultrasound energy is emitted, see diagram 38. The second quantity E3 of ultrasound energy can either be zero or have a minimal quantity. However, the quantity E3 is so low that emulsification is not possible. This quantity is preferably only so high that particles are supported by the small vibration of the needle according to the principle of a vibrating conveyor in travelling through the aspiration line.

If no occlusion is determined, only a minimal or no quantity of energy is supplied to the handpiece. If an occlusion is determined, a predetermined higher quantity of ultrasound energy is supplied to the handpiece, with this value being based on the established hardness of the particle to be broken up.

It is understood that the foregoing description is that of the preferred embodiments of the invention and that various changes and modifications may be made thereto without departing from the spirit and scope of the invention as defined in the appended claims.

What is claimed is:

1. A control apparatus for an ophthalmic surgical system including a handpiece for phacoemulsification of an eye lens, an energy source configured to output ultrasound energy to the handpiece, an aspiration line configured to conduct a fluid flow therethrough, said aspiration line being coupled to said handpiece and having a suction opening, the control apparatus comprising:
   a flow determination device configured to determine an actual value of a reduced fluid flow in said aspiration line;
   an occlusion determination device configured to determine whether an occlusion is present at said suction opening;
   an evaluation unit configured to determine said actual value of the reduced fluid flow in said aspiration line when said occlusion determination device has determined that an occlusion is present;
   said evaluation unit being further configured to determine a first value of the ultrasound energy to be outputted to said handpiece via said energy source in dependence upon said actual value of the reduced fluid flow; and,
   a control unit configured to control said energy source to output said first value of the ultrasound energy during the occlusion,
   wherein the fluid flow in said aspiration line has a nominal value when no occlusion is present; and, said evaluation unit is configured to determine a quotient of said actual value of the reduced fluid flow divided by said nominal value of the fluid flow in the aspiration line; and,
   wherein said evaluation unit is configured to determine an integral of said quotient as a function of time over a predetermined time duration.

2. The control apparatus of claim 1, wherein said control unit is further configured to control said energy source so as to cause said energy source to output a second value of the ultrasound energy when said occlusion determination device has determined that no occlusion is present; and, said second value of said ultrasound energy is lower than said first value thereof.

3. The control apparatus of claim 1, wherein the ophthalmic surgical system further includes an aspiration pump configured to draw a current; and, said occlusion determination device includes a measurement apparatus configured to measure the current drawn by said aspiration pump.

4. The control apparatus of claim 1, wherein the ophthalmic surgical system further includes an aspiration pump developing power; and, said occlusion determination device includes a measurement apparatus configured to measure the power of said pump.

5. The control apparatus of claim 1, wherein said occlusion determination device includes a measurement apparatus configured to measure the fluid flow in said aspiration line.

6. An ophthalmic surgical system comprising:
a handpiece for phacoemulsification of an eye lens;
an energy source configured to output ultrasound energy to said handpiece;
an aspiration line configured to conduct a fluid flow therethrough;
said aspiration line being coupled to said handpiece and having a suction opening; and,
a control apparatus including: a flow determination device configured to determine an actual value of a reduced fluid flow in said aspiration line; an occlusion determination device configured to determine whether an occlusion is present at said suction opening; an evaluation unit configured to determine said actual value of the fluid flow in said aspiration line when said occlusion determination device has determined that an occlusion is present; said evaluation unit being further configured to determine a first value of the ultrasound energy to be outputted to said handpiece via said energy source in dependence upon said actual value of the reduced fluid flow; and, a control unit configured to control said energy source to output said first value of the ultrasound energy during the occlusion,
wherein a fluid flow in said aspiration line has a nominal value when no occlusion is present; and, said evaluation unit is configured to determine a quotient of said actual value of the reduced fluid flow divided by said nominal value of the fluid flow in the aspiration line; and,
wherein said evaluation unit is configured to determine an integral of said quotient as a function of time over a predetermined time duration.

7. The ophthalmic surgical system of claim 6, wherein said control unit is further configured to control said energy source so as to cause said energy source to output a second value of said ultrasound energy when said occlusion determination device has determined that no occlusion is present; and, said second value of said ultrasound energy is lower than said first value thereof.

8. A control apparatus for an ophthalmic surgical system including a handpiece for phacoemulsification of an eye lens, an energy source configured to output ultrasound energy to the handpiece, an aspiration line configured to conduct a fluid flow therethrough, said aspiration line being coupled to said handpiece and having a suction opening, the control apparatus comprising:
a flow determination device configured to determine an actual value of a reduced fluid flow in said aspiration line;
an occlusion determination device configured to determine whether an occlusion is present at said suction opening;
an evaluation unit configured to determine said actual value of the reduced fluid flow in said aspiration line when said occlusion determination device has determined that an occlusion is present;
said evaluation unit being further configured to determine a first value of the ultrasound energy to be outputted to said handpiece via said energy source in dependence upon said actual value of the reduced fluid flow; and,
a control unit configured to control said energy source to output said first value of the ultrasound energy during the occlusion,
wherein said control unit is further configured to control said energy source so as to cause said energy source to output a second value of the ultrasound energy when said occlusion determination device has determined that no occlusion is present; and, said second value of said ultrasound energy is lower than said first value thereof,
wherein a fluid flow in said aspiration line has a nominal value when no occlusion is present; and, said evaluation unit is configured to determine an actual value of the reduced fluid flow divided by said nominal value of the fluid flow in the aspiration line; and,
wherein said evaluation unit is configured to determine an integral of said quotient as a function of time over a predetermined time duration.

* * * * *

UNITED STATES PATENT AND TRADEMARK OFFICE
CERTIFICATE OF CORRECTION

PATENT NO. : 9,144,517 B2  Page 1 of 1
APPLICATION NO. : 13/854075
DATED : September 29, 2015
INVENTOR(S) : C. Kuebler et al.

It is certified that error appears in the above-identified patent and that said Letters Patent is hereby corrected as shown below:

In the specification

In Column 1:
Line 55: delete "foe" and substitute -- be -- therefor.

In Column 3:
Line 2: delete "foe" and substitute -- be -- therefor.

In Column 4:
Line 7: delete "5" and substitute -- 6 -- therefor.
Line 10: insert -- 7 -- after "line".
Line 21: delete "hardiness" and substitute -- hardness -- therefor.

In Column 5:
Line 7: insert -- is -- after "$Q_{SET}$".
Line 19: delete "foe" and substitute -- be -- therefor.
Line 67: delete "quantify" and substitute -- quantity -- therefor.

Signed and Sealed this
Fifteenth Day of March, 2016

Michelle K. Lee
*Director of the United States Patent and Trademark Office*